US006641394B2

(12) United States Patent
Garman (10) Patent No.: US 6,641,394 B2
(45) Date of Patent: Nov. 4, 2003

(54) FLUID MATERIAL DELIVERY DEVICES AND METHODS

(75) Inventor: Gary T. Garman, La Verne, CA (US)

(73) Assignee: Ormco Corporation, Orange, CA (US)

( * ) Notice: Subject to any disclaimer, the term of this patent is extended or adjusted under 35 U.S.C. 154(b) by 0 days.

(21) Appl. No.: 09/928,587

(22) Filed: Aug. 13, 2001

(65) Prior Publication Data

US 2003/0031978 A1 Feb. 13, 2003

(51) Int. Cl.[7] .............................. A61G 5/02; A61C 5/04; A61C 17/06
(52) U.S. Cl. ................. 433/81; 433/90; 433/91
(58) Field of Search ................ 433/36, 81, 90, 433/91, 224; 222/335; 401/13; 604/35, 38, 173

(56) References Cited

U.S. PATENT DOCUMENTS

| | | | | | |
|---|---|---|---|---|---|
| 13,975 | A | * | 12/1855 | Buhler | 604/38 |
| 362,310 | A | * | 5/1887 | Parsons | 433/91 |
| 3,745,655 | A | * | 7/1973 | Malmin | 433/81 |
| 3,818,907 | A | * | 6/1974 | Walton | 604/38 |
| 3,871,099 | A | * | 3/1975 | Kahn | 433/81 |
| 4,021,921 | A | * | 5/1977 | Detaille | 433/81 |
| 4,109,653 | A | * | 8/1978 | Kozam et al. | 604/38 |
| 4,842,581 | A | * | 6/1989 | Davis | 604/38 |
| 4,993,947 | A | * | 2/1991 | Grosrey | 433/81 |
| 5,033,650 | A | * | 7/1991 | Colin et al. | 433/90 |
| 5,046,950 | A | | 9/1991 | Favonio | 433/81 |
| 5,171,146 | A | | 12/1992 | Guerci | 433/81 |
| 5,254,086 | A | * | 10/1993 | Palmer et al. | 604/38 |
| 5,295,828 | A | | 3/1994 | Grosrey | 433/81 |
| 5,860,949 | A | * | 1/1999 | Chen | 604/35 |
| 5,957,883 | A | * | 9/1999 | Lin | 604/38 |
| 6,386,871 | B1 | * | 5/2002 | Rossell | 433/81 |
| 2002/0072032 | A1 | * | 6/2002 | Senn et al. | 433/81 |

OTHER PUBLICATIONS

P. Portmann et al., *A Comparison between a New Vacuum Obturation Technique and Lateral Condensation: An In Vitro Study*, Journal of Endodontics, vol. 20, No. 6, Jun. 1994.

A. Lussi et al., *Obturation of Root Canals in Vivo with a New Vacuum Technique*, Journal of Endodontics, vol. 23, No. 10, Oct. 1997.

* cited by examiner

*Primary Examiner*—Todd E. Manahan
(74) *Attorney, Agent, or Firm*—Wood, Herron & Evans, L.L.P.

(57) ABSTRACT

Devices and methods for the application of materials to an interior space of a tooth, such as the extirpated pulp chamber and/or root canals of the tooth subsequent to root canal surgery. The device has one or more syringe-like pistons and associated chambers for drawing a vacuum within an extirpated pulp chamber and applying cleansing, sealing, and/or filler materials into the tooth under continued vacuum pressure to ensure complete and thorough application.

27 Claims, 10 Drawing Sheets

FLUID MATERIAL DELIVERY DEVICES AND METHODS

FIELD OF THE INVENTION

The present invention pertains to endodontic devices and methods, and more particularly to devices for and methods for cleaning and filling the pulp chamber of an endodontically extirpated root canal.

BACKGROUND OF THE INVENTION

Root canal therapy is a well-known procedure whereby the crown of a diseased tooth is opened to permit the canal to be cleaned and filled. In a normal procedure, pupal tissues are first removed from the canal, the canal is then cleaned and a sealer is applied, and finally the canal is filled with a filling material, generally gutta percha, synthetic gutta percha, or a composite filler.

A critical aspect of root canal therapy is the removal of all bacterial matter from the pupal chamber as well as the complete filling of the extirpated pupal chamber to prevent subsequent damage to the tooth or infection of the patient. Traditional methods of applying cleaning solutions and filler to extirpated root canals by injection or compaction are prone to the formation of air pockets within the canal, and thus complete cleansing and filling cannot be assured. Furthermore, the filling of canals by compaction methods is a time consuming and labor intensive process. To overcome these drawbacks, several devices have been proposed in which vacuum pressure is applied to an extirpated canal to eliminate air pockets and thus facilitate the complete distribution of cleansing and filling materials. Typical of such devices are those found in U.S. Pat. Nos. 5,046,950 to Favonio, No. 5,171,146 to Guerci, and No. 5,295,828 to Grosrey. While these devices have addressed the problems associated with the formation of air pockets, they generally employ pumps, valves, and other mechanical or electrical components, making them quite complex and therefore expensive to manufacture and maintain.

Accordingly, there is a need for an apparatus and methods for applying cleansers, sealants, and filler materials to extirpated root canals under vacuum pressure, but without the complexity and expense of devices previously proposed for such purposes.

BRIEF SUMMARY OF THE INVENTION

The present invention provides simplified devices and methods for the delivery of one or more fluids to an interior tooth space, such as extirpated root canals, under vacuum pressure in order to facilitate the complete and thorough treatment of the entire canal. Such fluids may, for example, be cleaning or rinsing fluids, digestive/sterilizing fluids, or filler materials, as well as other types of fluids. The invention provides various advantages over previous methods and apparatus used for cleansing and filling root canals under vacuum pressure. For example, the present invention eliminates or at least reduces the need for motorized pumps, valves, or other mechanical and electrical features. The invention thus provides a more compact and less complex device, which in turn is less expensive to purchase, use and maintain compared to previously available devices.

In a general aspect of the invention a syringe-like device has one or more chambers. In the two chamber embodiments, one chamber creates vacuum pressure in an extirpated pulp chamber and root canals and one dispenses a fluid material, such as a cleansing solution or filler material, into the evacuated chamber and canals. Each chamber has a dedicated conduit or passage to an applicator tip that can be placed in the opening of the pulp chamber so that the canal can be evacuated and filled with a desired substance. Each chamber is fitted with a plunger that has a piston for expelling air or other fluids, such as cleansing solution or filler material, as the plungers are advanced into their respective chambers. In the single chamber embodiment, the vacuum and dispensing functions are integrated into one chamber with one or more pistons separating respective dispensing and vacuum portions of the chamber.

The applicator tip of each embodiment is constructed to seal against an opening in the tooth to allow for adequate evacuation of the pulp chamber and root canals. The sealing is preferably provided by an o-ring type seal fixed to the end of the tip/nozzle, but may be substituted or augmented by a resilient tube or any other suitable sealing material capable of providing a substantially air-tight seal against a tooth. As one additional alternative, the seal may be formed from a small amount of filler or sealing material placed around the opening to the root canal. In a preferred embodiment of the invention, the chambers, the conduits leading to the tip, and the applicator tip itself are integrated into a single body.

In another aspect of the invention the device includes a plurality of chambers for dispensing multiple fluid materials into an evacuated pulp chamber and root canals. Accordingly, the device includes a plurality of plungers as described above, one for each chamber of the device. In this aspect of the invention, a plurality of cleansing solutions or filler materials may be applied to a root canal cavity either sequentially or at the same time.

In another aspect of the invention, an embodiment having a plurality of dispensing chambers includes structure for mixing the plurality of dispensed materials while they are being expelled from their respective chambers. The mixing structure may be a section of the applicator tip where the plurality of materials may freely mix, or the structure may include baffles to provide more thorough mixing of the dispensed materials. The mixing structure may be disposed within the tip of the apparatus or may be attached to the end of the tip. Other mixing apparatus may be used as well.

In yet another aspect of the invention, the plungers are connected together so that they can be uniformly advanced into their respective chambers in a single actuation of the plurality of plungers. In a preferred embodiment, the plunger rods associated with the dispensing chamber(s) are shorter in length or otherwise configured relative to the plunger rod for the vacuum chamber so that the creation of a vacuum within an extirpated tooth precedes the expulsion of cleansing solution or filler material into the tooth.

In another aspect of the invention, a method for cleansing, sealing, or filling the extirpated pulp chamber of a tooth includes positioning the device of the present invention to engage an opening of a tooth, advancing a first plunger to create a vacuum in an interior space of the tooth, and advancing the same plunger or a second plunger to dispense materials from the device into the interior space of the tooth.

Accordingly, a general objective of the present invention to provide a simple, compact and inexpensive device and a method of use for the effective cleansing and filling of extirpated root canals under vacuum pressure. These and other advantages, objectives and features of the invention will become more readily apparent to those of ordinary skill upon review of the following detailed description of an illustrative embodiment of the invention.

DETAILED DESCRIPTION OF THE PREFERRED EMBODIMENTS

Figure 1:
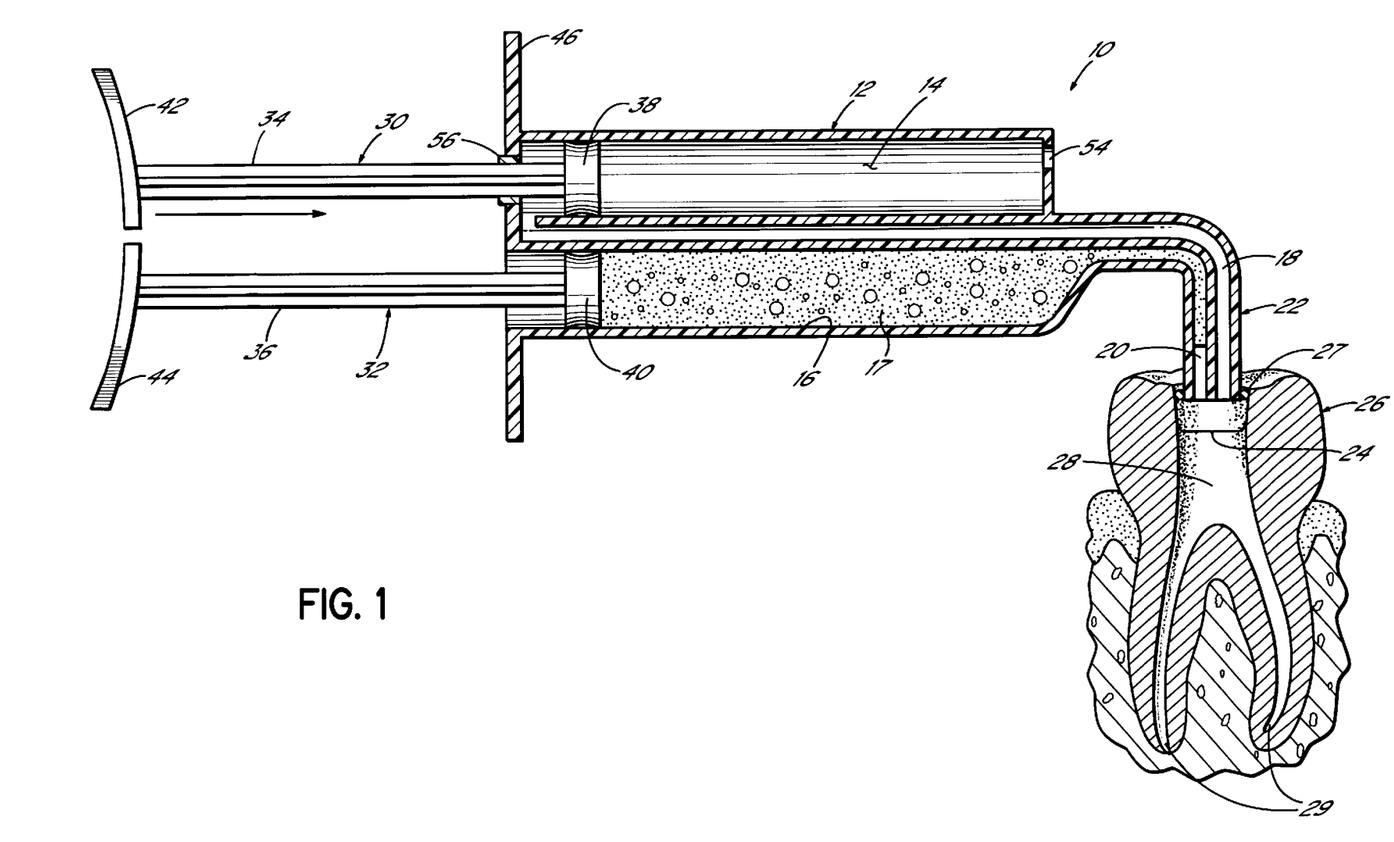
FIG. 1 is cross sectional view of one embodiment of the apparatus of the present invention generally taken along a longitudinal axis of the apparatus and a tooth.

Referring to FIG. 1, an apparatus 10 for filling extirpated root canals has a body 12 that includes a vacuum chamber 14 and a dispensing chamber 16 integrally formed with the body 10. Dispensing chamber 16 contains conventional filler material 17, such as one or more one-part fillers, composite filler materials, resin, gutta percha, or other filler materials as necessary or desired for a particular application. As additional non-limiting examples, cleaning or sterilizing solutions, such as water, sodium hypochlorite, EDTA or others, may be delivered with a device of this invention. Body 12 further includes a vacuum conduit 18 and a dispensing conduit 20, connected to vacuum chamber 14 and dispensing chamber 16 respectively. Conduits 18 and 20 join together to form an applicator tip 22 that is shaped preferably to fit within an opening 24 formed in a tooth 26. However, it need not actually extend into opening 24 as long as an adequate seal is formed. In the preferred embodiment, a seal 27, schematically illustrated as an O-ring type seal, is affixed around the outside of tip 22 to seal pulp chamber 28 and root canals 29 of the tooth 26 in a manner allowing a vacuum or negative pressure condition to exist therein. It will be appreciated that, while an O-ring is illustrated for clarity, other conventional dental sealing materials may be applied against tip 22 and tooth 26 to maintain an adequately sealed condition during use of device 10.

Plungers 30 and 32 are comprised of plunger rods 34 and 36, pistons 38 and 40, and thumb pads 42 and 44. Pistons 38 and 40 are respectively disposed within vacuum chamber 14 and dispensing chamber 16 and are constructed to slidably seal against the interior walls of their respective chambers 14, 16. Plunger rods 34 and 36 extend outside of the body 12 from within chambers 14 and 16 and terminate in thumb pads 42 and 44 such that pistons 38 and 40 may be independently urged along the vacuum and dispensing chambers 14 and 16 when pressure is applied to the thumb pads 42 and 44. Body 12 also includes a flange or other finger grip 46 that can be gripped by an operator to make it easier to apply pressure to thumb pads 42 and 44.

Figure 1A:
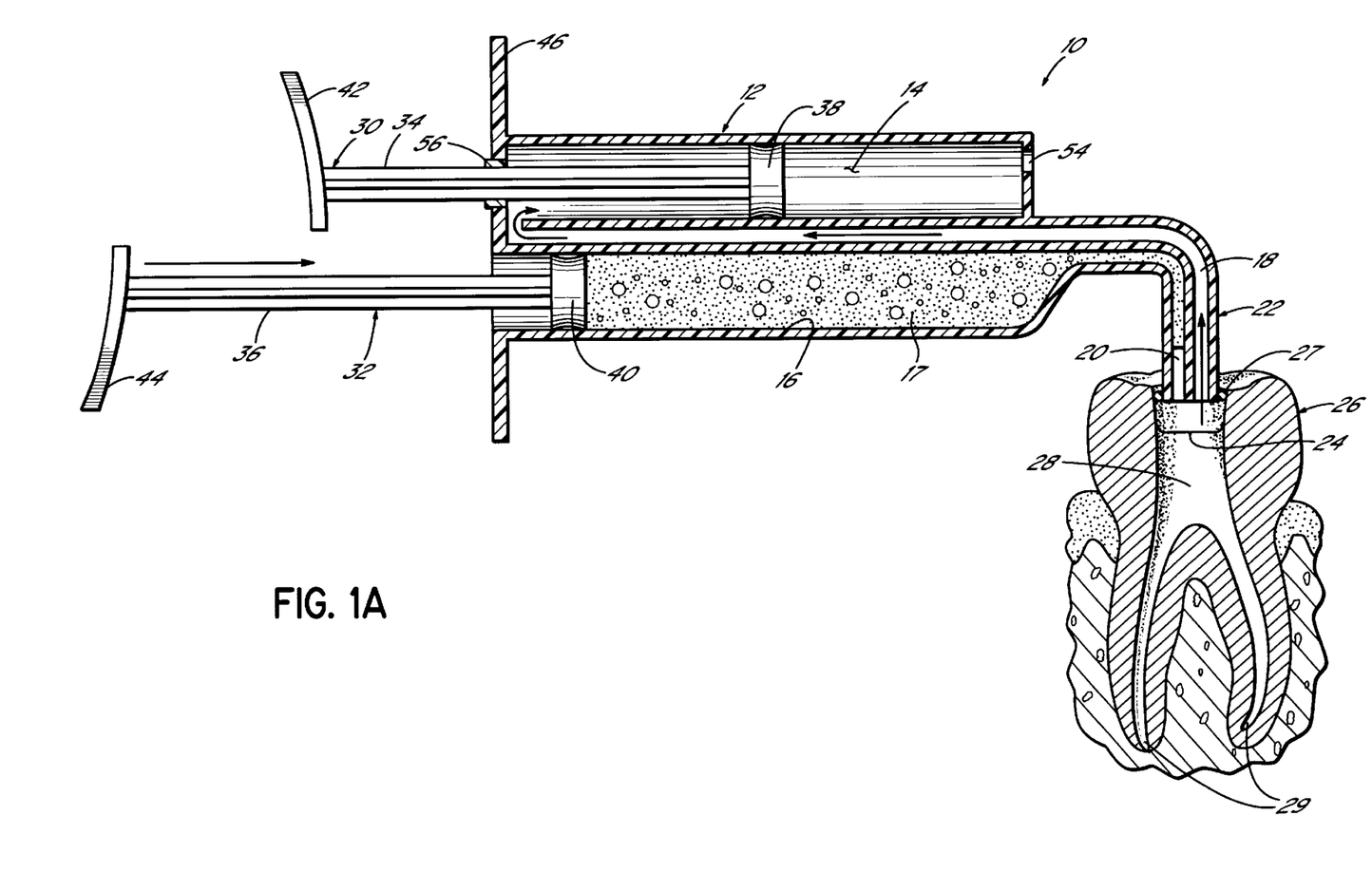
FIG. 1A is a cross sectional view similar to FIG. 1, but illustrating the apparatus in use to evacuate the pulp chamber of the tooth.

To operate apparatus 10, as illustrated in the position shown in FIG. 1, the operator first grasps apparatus 10 with flange 46 and thumb pad 42 between their fingers and thumb. Thumb pad 42 and plunger 30 are then depressed to develop a partial vacuum within pulp chamber 28 and root canals 29 as shown in FIG. 1A. As vacuum piston 38 is moved through vacuum chamber 14, the effective volume on the plunger rod side of the piston 38 is increased, creating a suction in vacuum conduit 18. This, in turn, creates partial vacuum inside sealed pulp chamber 28 of tooth 26 prior to expulsion of filler material 17 from dispensing chamber 16. A breather hole or vent 54 of vacuum chamber 14 allows air to escape from the chamber 14 as piston 38 is advanced. On the opposite side of piston 38, vacuum pressure in the vacuum chamber 14 is maintained by a seal 56 through which plunger 30 protrudes. After vacuum has been drawn in pulp chamber 28, plunger 32 is depressed using thumb pad 44. Piston 40 thereby expels filler material 17 through conduit 20 and into pulp chamber 28. After pulp chamber 28 is filled, apparatus 10 is removed by detaching tip 22 and the outer end of opening 24 then may be sealed or closed in a conventional manner.

Figure 1B:
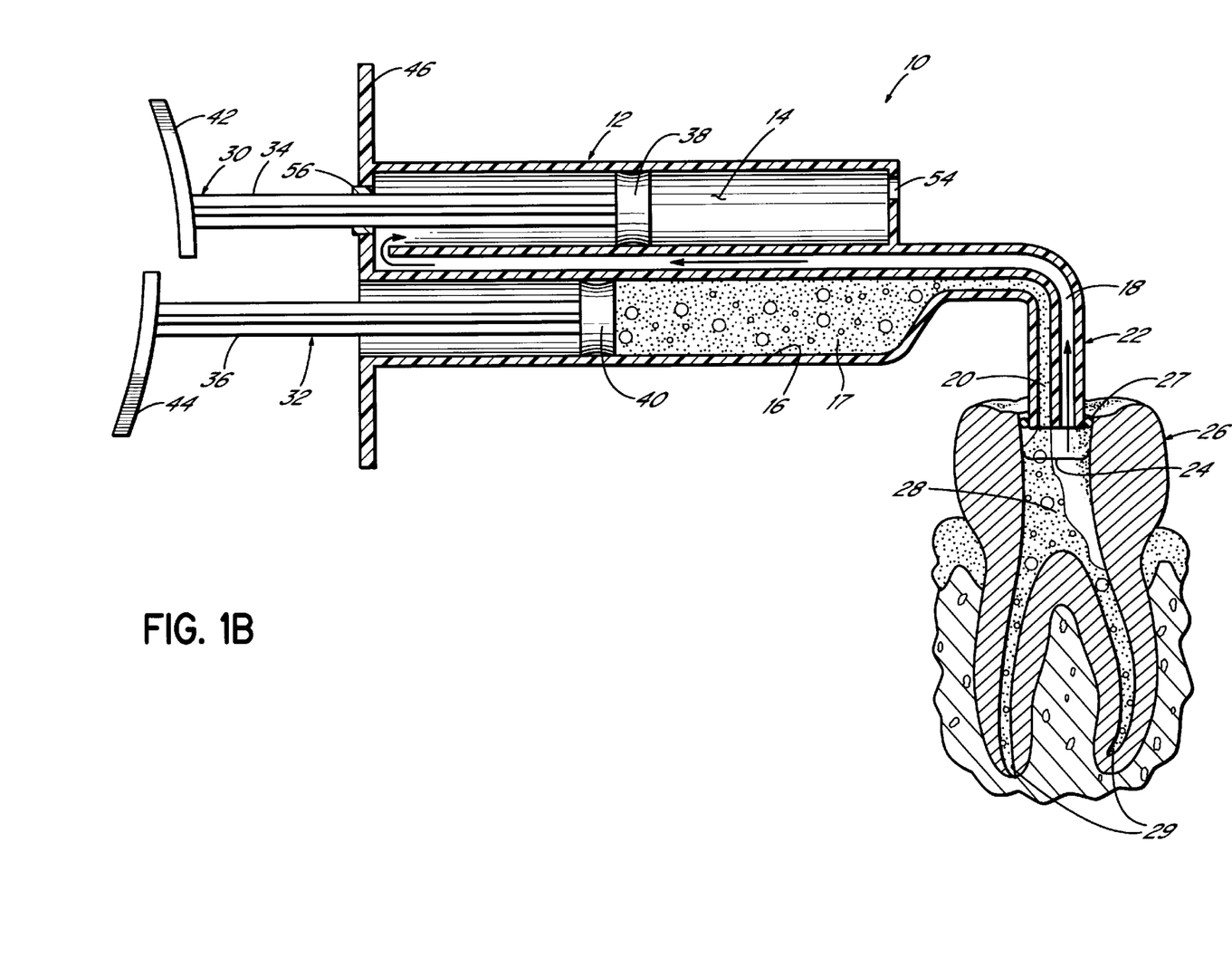
FIG. 1B is a cross sectional view similar to FIG. 1A, but illustrating the further step of filling the pulp chamber with filler material.
Figure 2:
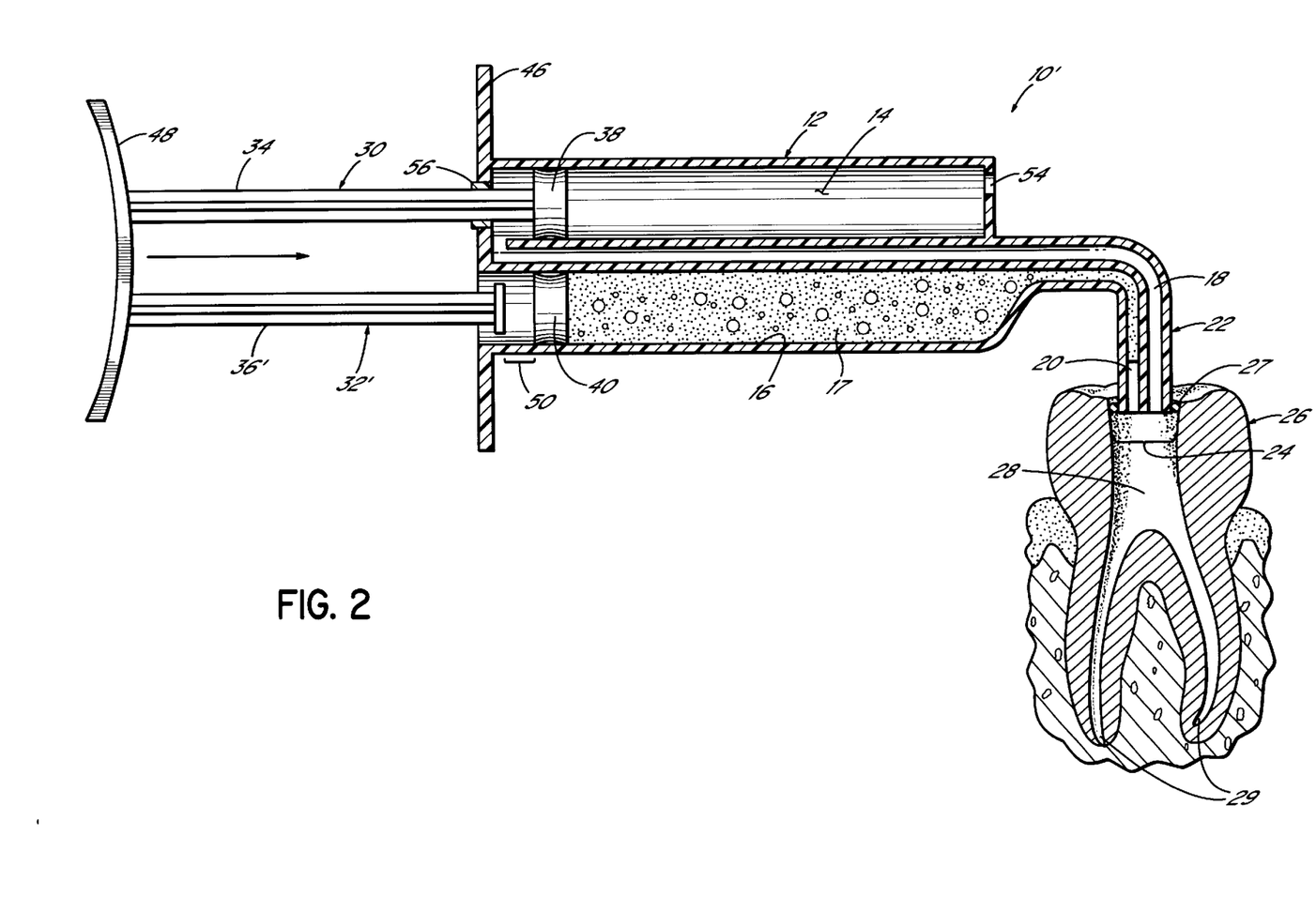
FIG. 2 is a cross sectional view similar to FIG. 1, but illustrating a second embodiment of the present invention.
Figure 2A:
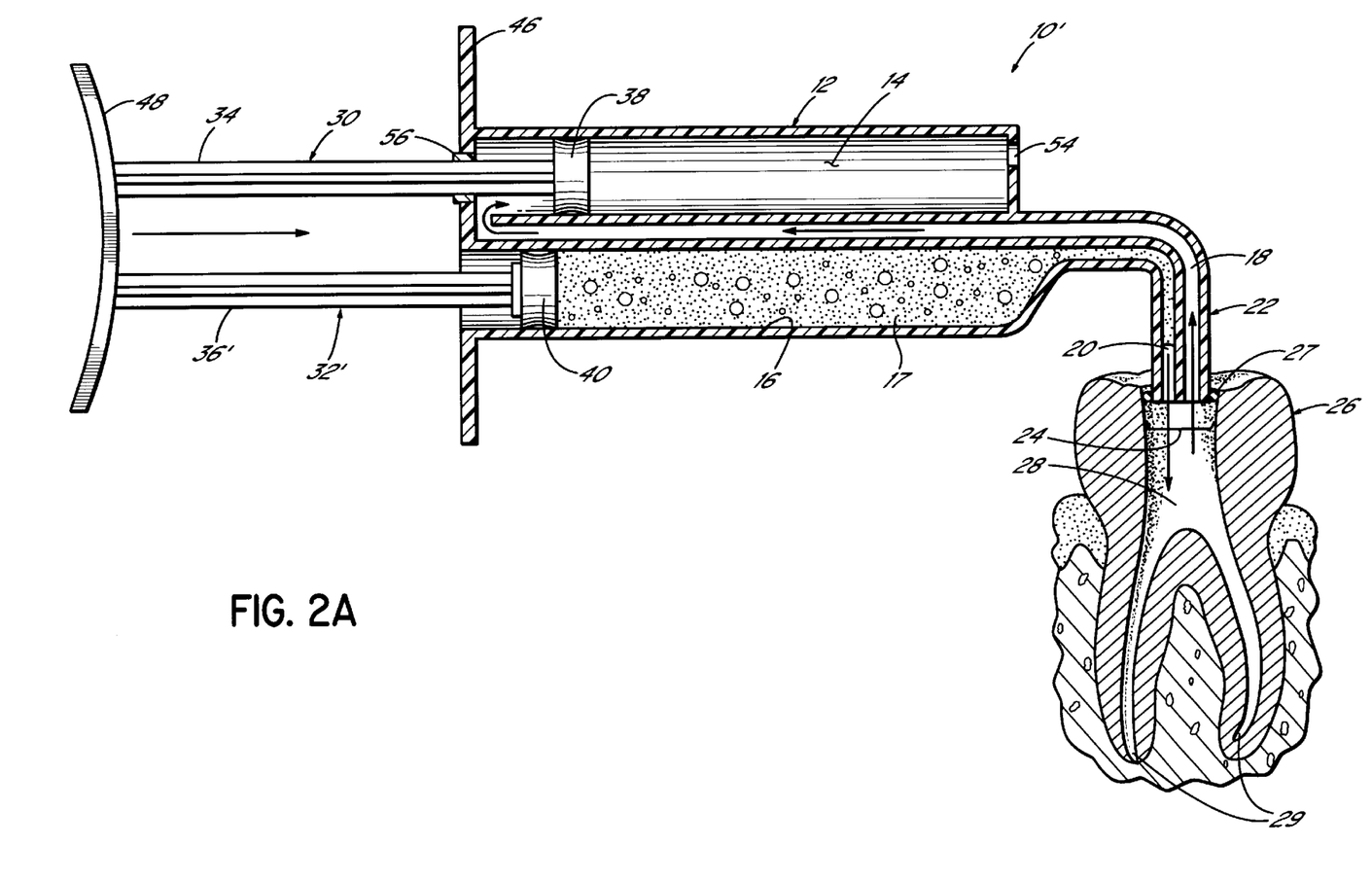
FIG. 2A is a cross sectional view similar to FIG. 2, but showing an initial actuation of the plungers to create vacuum pressure within the pulp chamber of a tooth.
Figure 2B:
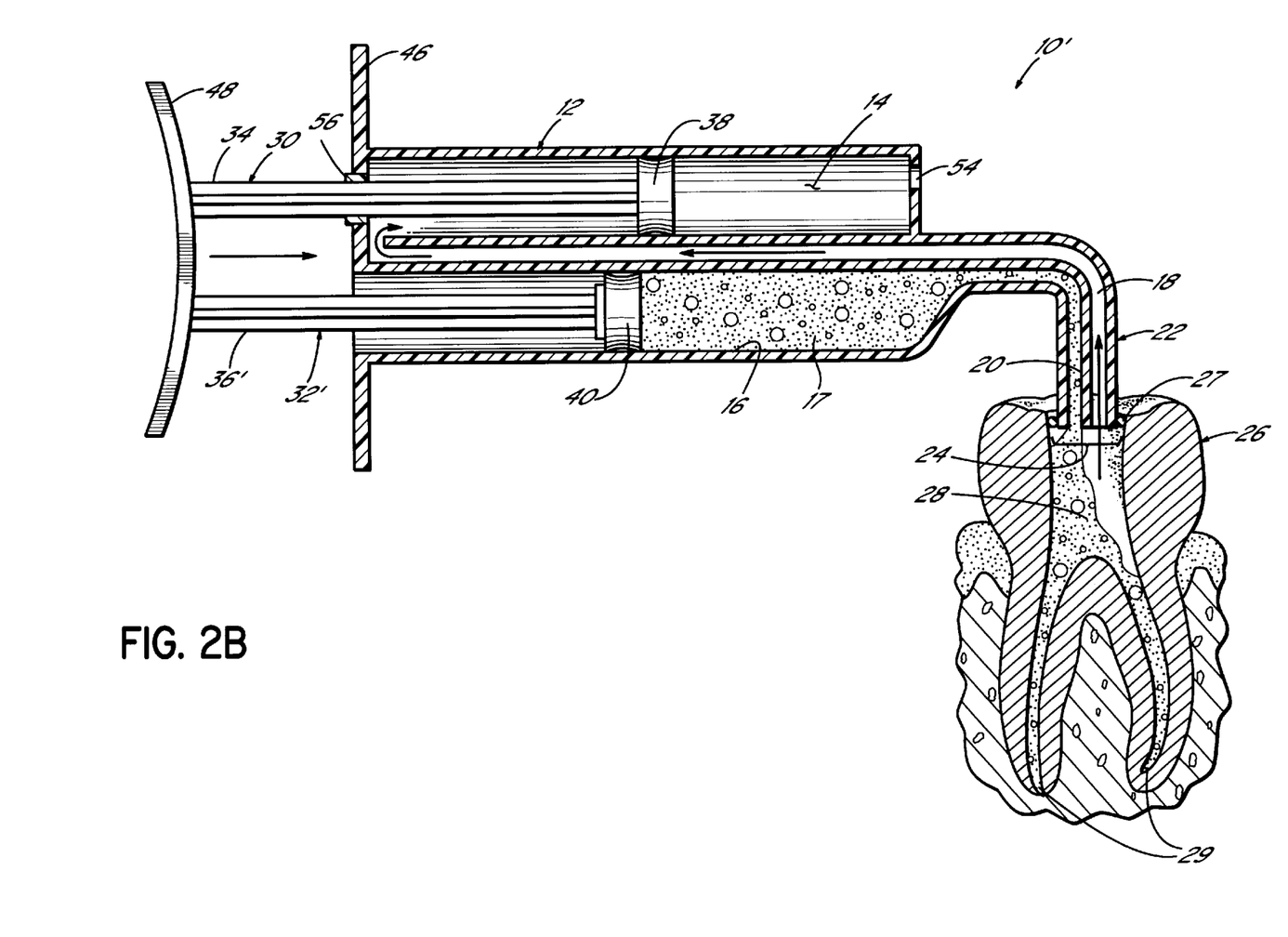
FIG. 2B is a cross sectional view similar to FIG. 2A, but showing further actuation of the plungers to dispense filler material into the pulp chamber.

FIGS. 2, 2A and 2B illustrate an alternative apparatus 10' according to the invention, wherein plungers 30 and 32' are connected via a common thumb pad 48 so that both plungers may be advanced in unison. In FIGS. 2, 2A and 2B, like numerals represent common elements of structure with the embodiment of FIGS. 1, 1A and 1B. Reference numerals with prime (') marks represent structure that is somewhat changed as compared to the first embodiment, as will be apparent from the illustrations. Plunger rod 36' is detached from piston 40 and is shorter than plunger rod 34 disposed in the vacuum chamber 14 so that a gap 50 is created between rod 36' and piston 40 in dispensing chamber 16, thereby causing a delay between the actuation of pistons 38 and 40 when pressure is applied to thumb pad 48 to uniformly advance plungers 30 and 32'.

To fill an extirpated pulp chamber 28 and root canal 29 of tooth 26 apparatus 10' is positioned proximate tooth 26 such that the tip 22 substantially fills an opening 24 to the pulp chamber 28. Tip 22 again includes an appropriate seal 27 located at its distal end for engaging tooth 26 and creating a substantially air-tight seal between the ends of the conduits 18 and 20 and the pulp chamber 28. With the tip 22 in place, an operator applies pressure to thumb pad 48, using flange 46 for leverage, thereby uniformly advancing plunger rods 30 and 32'. Due to gap 50, vacuum plunger rod 34 urges vacuum piston 38 through vacuum chamber 14 before dispensing plunger rod 36' engages dispensing piston 40. As vacuum piston 38 is moved through vacuum chamber 14, the effective volume on the plunger rod side of the piston 40 is increased, creating a suction in vacuum conduit 18, which in turn creates a partial vacuum inside sealed pulp chamber 28 of tooth 26 prior to expulsion of filler material 17 from dispensing chamber 16. A breather hole 54 of vacuum chamber 14 allows air to escape from the chamber 14 as piston 38 is advanced. On the opposite side of piston 38, vacuum pressure in the vacuum chamber 14 is maintained by a seal 56 through which plunger 30 protrudes. Those of ordinary skill will, after reviewing this illustrative embodiment, realize that other configurations of the plunger rods, chambers and/or pistons, as well as the positioning of the filler material or other fluid material(s) may be changed while still resulting in the desired delay.

As shown in FIGS. 2A and 2B, when dispensing plunger rod 36' contacts dispensing piston 40 after covering the distance created by gap 50, piston 40 is urged through the dispensing chamber 16 to expel the filler material 17 from chamber 16 through dispensing conduit 20 and into pulp chamber 28, while vacuum plunger 30 continues to advance and, therefore, maintain vacuum pressure in the pulp chamber 28. FIG. 2B depicts the filling of pulp chamber 28 and root canals 29 with the contents 17 of the dispensing chamber 16 under continued vacuum pressure caused by the advance of vacuum piston 38 through vacuum chamber 14. It will be appreciated that the continued application of vacuum pressure to pulp chamber 28 and root canals 29 as these areas are being filled serves to eliminate air pockets therein and to promote complete filling of the root canals 29 and pump chamber 28 with material 17. Various materials 17 may be used depending on the purpose of the procedure. For example, to cleanse or apply sealant to an extirpated pulp chamber, the same process described above or below is followed, but dispensing chamber 16 is filled with cleaning solution or sealant as appropriate.

Figure 3:
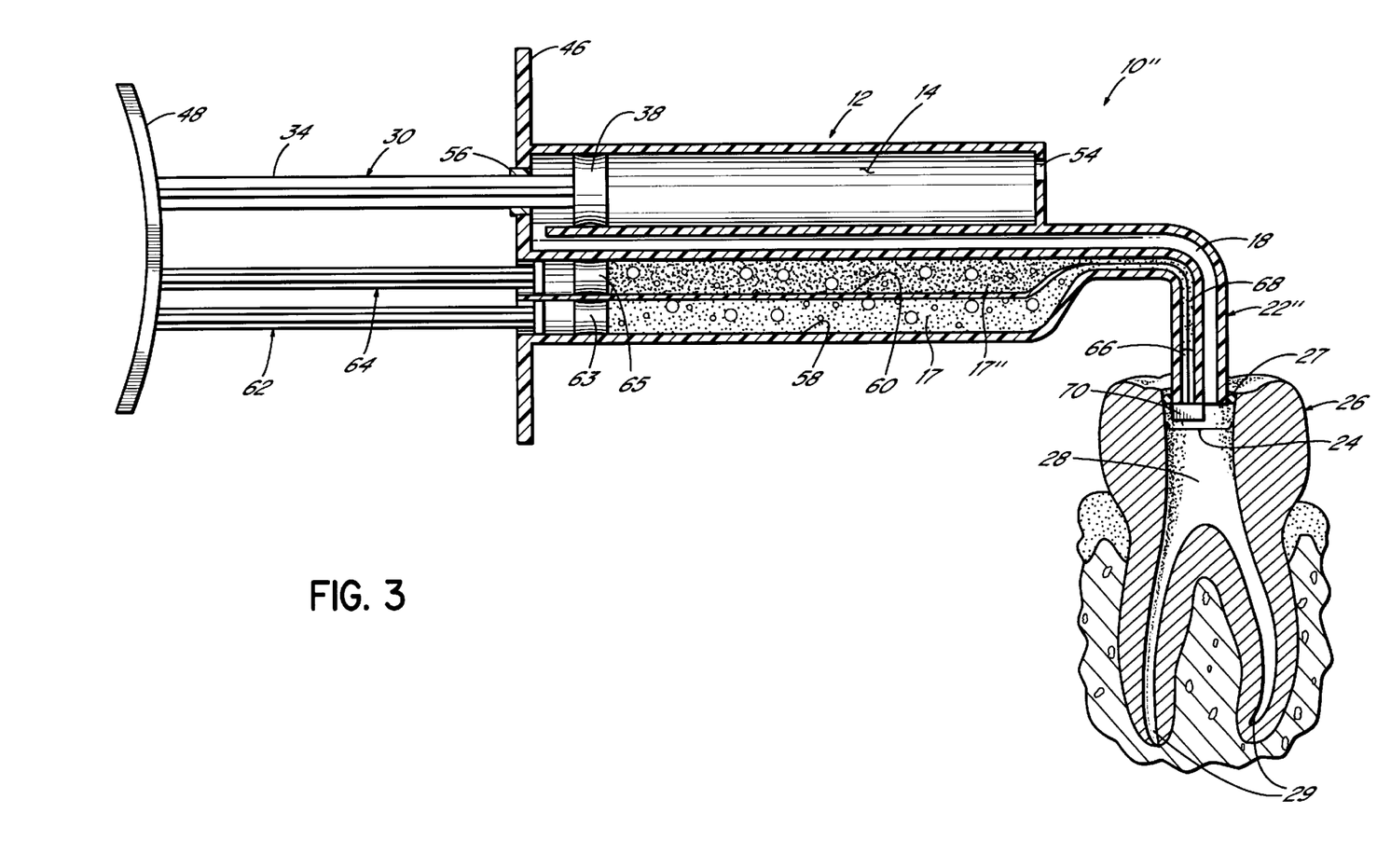
FIG. 3 is a cross sectional view similar to FIGS. 1 and 2, but illustrating a third alternative embodiment of the present invention having a plurality of dispensing chambers and plungers.

FIG. 3 depicts another alternative embodiment of the present invention. Again, in this embodiment, elements with like reference numerals as compared with the first two embodiments represent like structure, while elements with double prime (") marks are corresponding elements that have been somewhat modified as will be apparent. Detailed description of like elements is contained above and, therefore, these descriptions are not repeated. In this third embodiment, apparatus 10" includes multiple dispensing chambers 58 and 60 with corresponding plungers 62 and 64, dispensing pistons 63 and 65, and dispensing conduits 66 and 68 with tip 22" for dispensing several different materials from the multiple dispensing chambers 58 and 60 at the same time. A mixing baffle 70 is attached to the tip 22" of apparatus 10", proximate the exit of the plurality of dispensing conduits 66 and 68 to mix the dispensed materials as they enter the pulp chamber 28. Apparatus 10" operates as described above with regard to FIGS. 2, 2A and 2B, with the exception that it is capable of dispensing multiple types of materials 17, 17" from the dispensing chambers and mixing those materials 17, 17" prior to their discharge into pulp chamber 28 of tooth 26. The operation of this embodiment is as described for the second embodiment.

Figure 4:
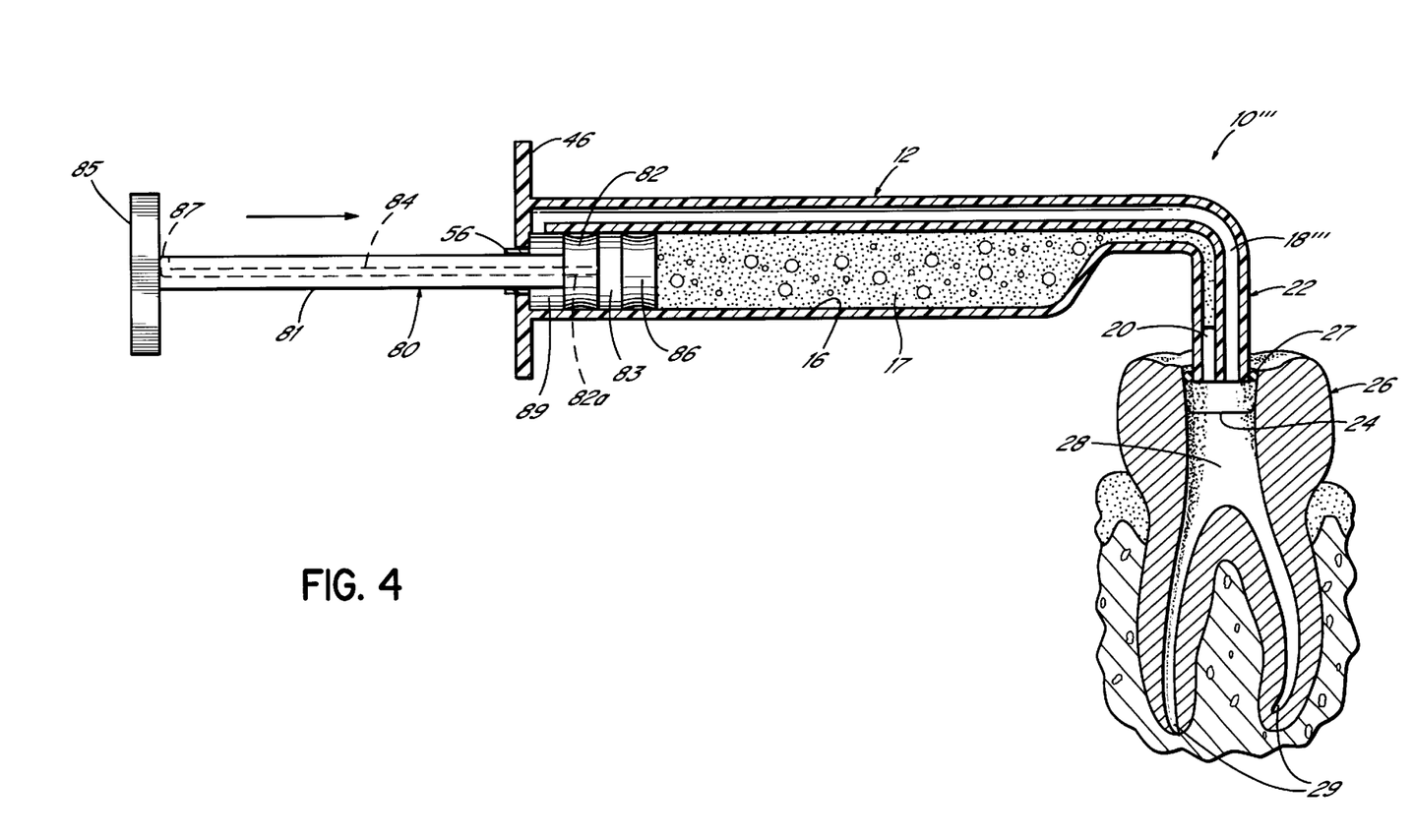
FIG. 4 is a cross sectional view similar to FIGS. 1, 2 and 3, but illustrating a fourth alternative embodiment of the present invention that eliminates the use of a separate vacuum space.
Figure 4A:
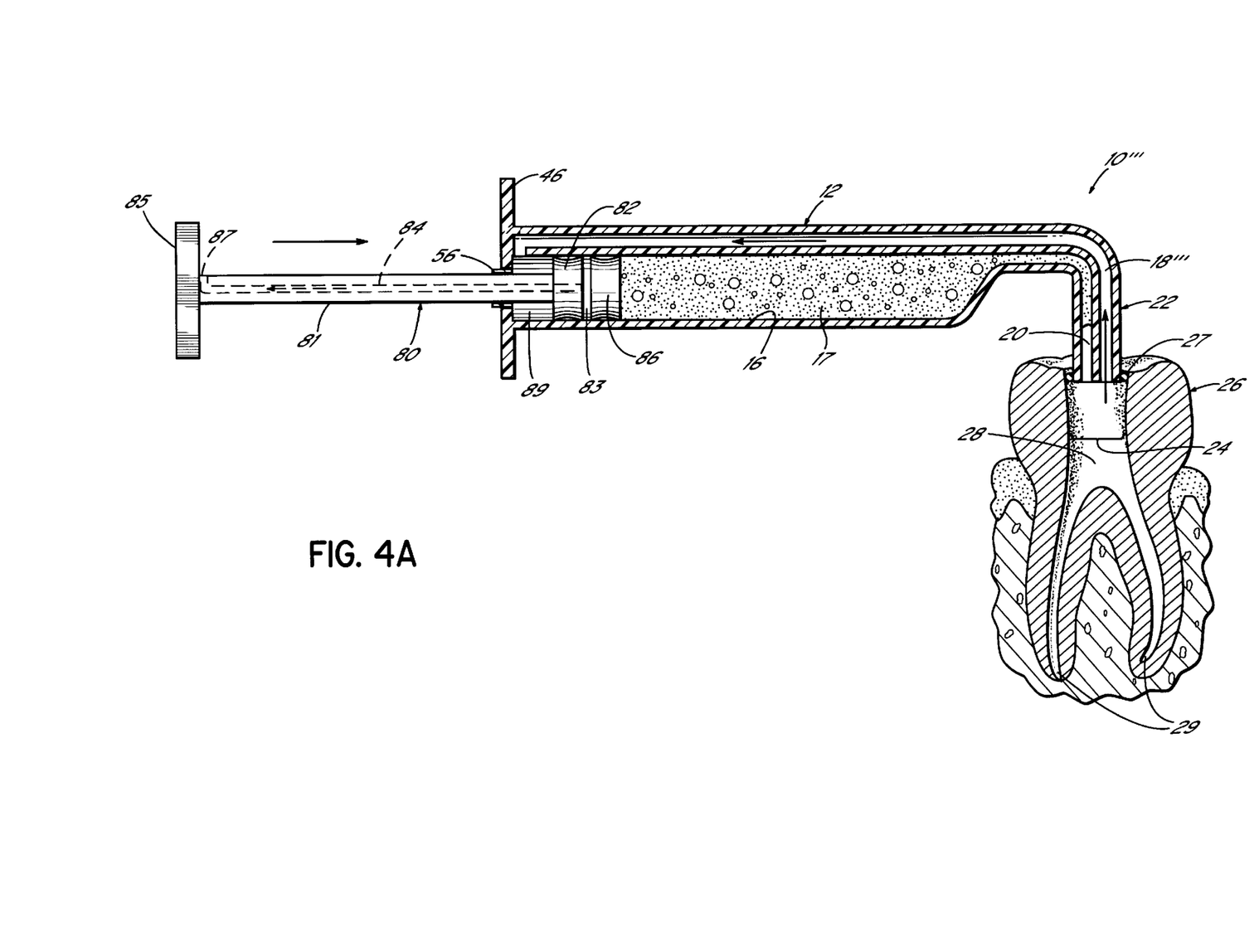
FIG. 4A is a cross sectional view similar to FIG. 4, but illustrating the apparatus in use to evacuate the pulp chamber of the tooth.
Figure 4B:
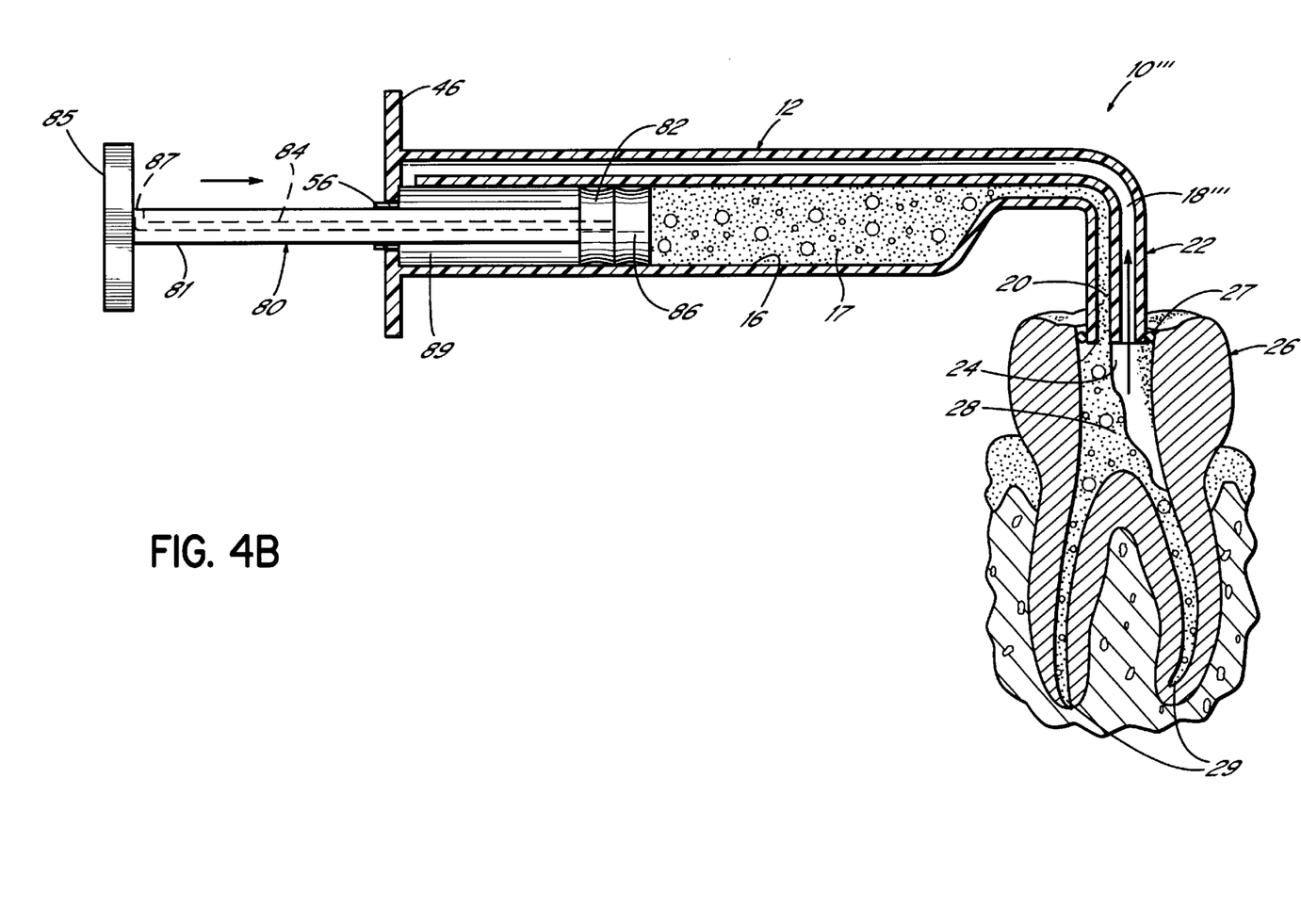
FIG. 4B is a cross sectional view similar to FIG. 4A, but illustrating the further step of filling the pulp chamber with filler material.

FIGS. 4, 4A and 4B illustrate another alternative embodiment of the current invention. Again, as in previous embodiments, elements with like reference numerals as compared to the first three embodiments represent like structure, while elements with the triple prime ('") marks are corresponding elements that have been somewhat modified as will be apparent. Detailed description of like elements is contained above and, therefore, these descriptions will not be repeated. In this embodiment, apparatus 10'" contains a single dispensing chamber 16 with pistons 82 and 86, separated by a space 83. Pistons 82 and 86 are designed to be slidably sealed against the interior walls of chamber 16 while piston 82 is also attached to or, at least, capable of being moved by plunger 80. Plunger rod 81 contains a venting port 84 that is oriented coaxially along the long axis of the plunger rod 81. This port 84 communicates with the space 83 at one end of the plunger 80 via a hole 82a in the center of piston 82. Venting port 84 vents to the outside of apparatus 10'" through vent hole 87 located just beneath thumb pad 85 and along the outer edge of plunger rod 81. Note that vacuum chamber 14 has been entirely disposed of in this embodiment and has been replaced with an extended vacuum conduit 18'".

In order to facilitate the filling of a pulp chamber 28 and root canals 29, apparatus 10'" is positioned relative to tooth 26 such that tip 22 and seal 27 engage the tooth opening 24 and an air tight seal is formed.

While tip 22 is engaged, thumb pad 85 is depressed using flange 46 for leverage. This initially advances only piston 82. As piston 82 is advanced, air from space 83 is forced out of venting port 84 and expelled to the atmosphere via vent hole 87 (FIG. 4A). As space 83 is evacuated, a pre-vacuum is created in a space 89 located on the plunger side of piston 82 and in communication with the vacuum conduit 18'". The effect of this pre-vacuum is to draw the air from the pulp chamber 28 and the root canals 29 through the extended vacuum conduit 18'" so as to evacuate the tooth prior to the movement of the filler material 17 (see FIG. 4A). Space 83 essentially acts to delay the movement of piston 86 (and therefore filler material 17) until space 83 is completely evacuated and the pulp chamber 28 and root canals 29 are at least substantially evacuated.

Once space 83 is evacuated, piston 82 abuts piston 86 (FIG. 4B). Continued pressure on thumb pad 85 simultaneously advances pistons 82 and 86. The vacuum in the pulp chamber 28 and root canals 29 is thereby further increased as air is drawn into the emptied dispensing chamber 16 on the plunger side of advancing pistons 82 and 86. This action causes the expulsion of filler material 17 from the dispensing chamber 16 into the evacuated pulp chamber 28 and root canals 29 until chamber 28 and canals 29 are completely filled.

It will be appreciated that pistons 82, 86 may be replaced by a single piston which simultaneously dispenses filler material 17, or another fluid material in accordance with the invention, while evacuating the interior of tooth 26. In other words, there would be no pre-vacuum provided as in the embodiment shown in FIGS. 4, 4A and 4B. In addition, the embodiments utilizing one or more pistons in the same dispensing chamber may also be adapted to multiple dispensing chambers, for example, each having a different fluid material. In such an embodiment, a vacuum conduit would communicate with the back side or plunger side of each dispensing chamber.

While the present invention has been illustrated by a description of preferred embodiments and while the embodiments have been described in considerable detail, it is not the intention of the Applicant to restrict or in any way limit the scope of the appended claims to such detail. Additional advantages, modifications and adaptations of this invention will become apparent to those skilled in the art upon reviewing this disclosure. The various features of each embodiment may be combined with one or more features of other embodiments, or other features as desired in the art. The invention in its broader aspects is therefore not limited to the specific details, representative apparatus and method as shown and described. The invention itself should only be defined by the appended claims, wherein I claim:

What is claimed is:

1. A device for delivering a fluid to an interior space of a tooth, the device comprising:

vacuum chamber;

a dispensing chamber adapted to receive a fluid material;

a first conduit having a first end in fluid communication with said vacuum chamber and a second open end;

a second conduit having a first end in fluid communication with said dispensing chamber and a second open end;

a first plunger disposed within said vacuum chamber and configured for movement to draw air into said vacuum chamber through said second open end of said first conduit;

a second plunger disposed within said dispensing chamber and configured for movement to discharge the fluid material from said dispensing chamber through said second open end of said second conduit; and a sealing surface disposed proximate said second open ends of said first and second conduits and operative to at least assist in forming a substantially air-tight seal between the first and second conduits and the interior space of the tooth when said first and second conduits are positioned in fluid communication with the interior space, wherein the vacuum chamber and the dispensing chamber are positioned within a unitary body configured for handheld use on a patient.

2. The device of claim 1, wherein the sealing surface is on an annular seal attached to the second ends of said first and second conduits.

3. The device of claim 1, wherein the vacuum chamber and the dispensing chamber are positioned within an integrally formed body.

4. The device of claim 1, wherein proximal ends of said first and second plungers are connected such that said first and second plungers move in unison when depressed into the vacuum and dispensing chambers.

5. The device of claim 4, wherein said first and second pistons are configured such that, when the first and second plungers are depressed in unison, said first plunger begins to create a vacuum in the pulp chamber prior to the expulsion of filler material from said second chamber and second conduit into the interior space of the tooth.

6. The device of claim 1, wherein the first and second plungers further comprise manually operated plungers with at least one thumb pad coupled at proximal ends thereof, and said vacuum and dispensing chambers are positioned in a body having at least one finger grip for allowing leverage to be applied by an operator as said first and second plungers are manually depressed into said vacuum and dispensing chambers.

7. The device of claim 1, wherein said first and second plungers are independently movable into said vacuum and dispensing chambers.

8. The device of claim 1, wherein said vacuum chamber and said dispensing chamber are coupled in side-by-side relation.

9. The device of claim 1, wherein said dispensing chamber contains said fluid material.

10. The device of claim 9, wherein said fluid material is a filler material.

11. The device of claim 9, wherein said fluid material is a cleaning fluid.

12. The device of claim 9, wherein said fluid material is a sterilizing fluid.

13. A device for delivering a fluid to an interior space of a tooth, the device comprising:

a vacuum chamber;

a plurality of dispensing chambers adapted to receive at least a corresponding plurality of fluid materials;

a vacuum conduit having a first end in fluid communication with said vacuum chamber and a second open end;

a plurality of dispensing conduits having first ends respectively in fluid communication with said plurality of dispensing chambers and further having respective second open ends;

a vacuum plunger disposed within said vacuum chamber and configured for movement to draw air into said vacuum chamber through said second open end of said vacuum conduit;

a plurality of dispensing plungers respectively disposed within said plurality of dispensing chambers, each dispensing plunger configured for movement to discharge one of the fluid materials from one of said dispensing chambers through one of said second open ends of a corresponding one of said dispensing conduits; and a sealing surface disposed proximate said second open ends of said vacuum and dispensing conduits and operative to at least assist in forming a substantially air-tight seal between the vacuum and dispensing conduits and the interior space of the tooth when the vacuum and dispensing conduits are positioned in fluid communication with the interior space, wherein the vacuum chamber and the dispensing chambers are formed within a unitary body configured for handheld use on a patient.

14. The device of claim 13 further comprising mixing structure in fluid communication with said plurality of dispensing conduits and operative to mix the plurality of fluid materials prior to discharge into the interior space of the tooth.

15. The device of claim 13, wherein the sealing surface is on an annular seal attached to the second ends of said vacuum conduit and the plurality of dispensing conduits.

16. The device of claim 13, wherein the vacuum chamber and the dispensing chambers are positioned within an integrally formed body.

17. The device of claim 13, wherein proximal ends of said vacuum and dispensing plungers are connected such that said vacuum and dispensing plungers move in unison when depressed into said vacuum and dispensing chambers.

18. The device of claim 17, wherein said dispensing plungers are configured such that, when said vacuum and dispensing plungers are depressed in unison, said vacuum plunger begins to create a vacuum in the interior space prior to the expulsion of filler material from said dispensing chambers and dispensing conduits into the interior space of the tooth.

19. The device of claim 13, wherein said vacuum and dispensing plungers further comprise manually operated plungers with at least one thumb pad coupled at proximal ends thereof, and said vacuum and dispensing chambers are positioned in a body having at least one finger grip for allowing leverage to be applied by an operator as said vacuum and dispensing plungers are manually depressed into said vacuum and dispensing chambers.

20. The device of claim 13, wherein said vacuum and dispensing plungers are independently movable into said vacuum and dispensing chambers.

21. The device of claim 13, wherein said vacuum chamber and said dispensing chambers are coupled in side-by-side relation.

22. The device of claim 13, wherein said dispensing chambers respectively contain said fluid materials.

23. A method of delivering a fluid material to an interior space of a tooth using a device including a first piston disposed within a first chamber and a second piston disposed within a second chamber containing the fluid material, the first and second chambers being formed within a unitary body configured for handheld use on a patient, the method comprising:

positioning the device to engage an opening of the tooth leading to the interior space with the first and second chambers in sealed fluid communication with the interior space;

manually holding the unitary body while moving the first piston to at least partially evacuate the interior space; and manually holding the unitary body while moving the second piston to dispense the fluid material from the second chamber into the interior space.

24. The method of claim 23, further comprising:

providing the device with a third chamber filled with a second fluid material and a third piston disposed with the third chamber, sealing the third chamber in fluid communication with the interior space, and moving the third piston into the third chamber to dispense the second fluid material into the interior space.

25. The method of claim 24, further comprising:

mixing the first and second fluid materials prior to dispensing the fluid materials into the interior space.

26. The method of claim 23, wherein the interior space includes the root canals of the tooth.

27. The method of claim 23, wherein the interior space includes the pulp chamber of the tooth.

* * * * *